United States Patent
Maswadeh et al.

[11] Patent Number: 5,856,616
[45] Date of Patent: Jan. 5, 1999

[54] HAND-HELD TEMPERATURE PROGRAMMABLE MODULAR GAS CHROMATOGRAPH

[75] Inventors: Waleed M. Maswadeh, Edgewood; A. Peter Snyder, Bel Air, both of Md.

[73] Assignee: The United States of America as represented by the Secretary of the Army, Washington, D.C.

[21] Appl. No.: 821,893

[22] Filed: Mar. 21, 1997

[51] Int. Cl.[6] .......................... G01N 30/04; G01N 30/02
[52] U.S. Cl. ............................. 73/23.42; 422/89
[58] Field of Search .................................. 95/87; 96/102, 96/105; 73/23.41, 23.42, 23.35; 422/89

[56] References Cited

U.S. PATENT DOCUMENTS

| | | | |
|---|---|---|---|
| H1563 | 7/1996 | Snyder et al. | 435/7.32 |
| 4,471,647 | 9/1984 | Jerman et al. | 73/23 |
| 4,474,889 | 10/1984 | Terry et al. | 436/161 |
| 4,935,040 | 6/1990 | Goedert | 55/197 |
| 5,005,399 | 4/1991 | Holtzclaw et al. | 73/23.39 |
| 5,114,439 | 5/1992 | Yost et al. | 55/20 |
| 5,135,549 | 8/1992 | Phillips et al. | 55/67 |
| 5,162,649 | 11/1992 | Burke | 250/287 |
| 5,227,628 | 7/1993 | Turner | 250/286 |
| 5,268,302 | 12/1993 | Rounbehler et al. | 436/96 |
| 5,310,681 | 5/1994 | Rounbehler et al. | 436/106 |
| 5,313,061 | 5/1994 | Drew et al. | 250/281 |
| 5,437,179 | 8/1995 | Wiegand et al. | 73/23.35 |
| 5,583,281 | 12/1996 | Yu | 73/23.42 |
| 5,589,630 | 12/1996 | Wiegand et al. | 73/23.35 |
| 5,611,846 | 3/1997 | Overton et al. | 96/102 |

Primary Examiner—Hezron Williams
Assistant Examiner—Jay L. Politzer
Attorney, Agent, or Firm—Edward L. Stolarun; Ulysses John Biffoni

[57] ABSTRACT

A hand-portable, modular and temperature programmable gas chromatography apparatus having reduced power consumption requirements is disclosed. The gas chromatography module includes a ring oven for housing a gas chromatography capillary column and programmable means for controlling the temperature of said column within the ring. The gas chromatography capillary column includes a sampling end and an effluent end. The sampling end of the GC capillary column is in fluid communication with a sampling nozzle and a vacuum pulse generating means. The vacuum generating means generates a sample pulse and directs the sample pulse to the sampling end of the gas chromatography capillary column during sample injection mode. During standby mode only clean dry air is directed to the column. The module is also easily interfaced with secondary sample detection or analysis instruments so that additional identification dimensions can added.

10 Claims, 8 Drawing Sheets

HAND-HELD TEMPERATURE PROGRAMMABLE MODULAR GAS CHROMATOGRAPH

GOVERNMENT INTEREST

The invention described herein may be manufactured, licensed, and used by or for the U.S. Government.

BACKGROUND OF THE INVENTION

1. Field of the Invention

The present invention relates to a gas chromatograph system of reduced size, weight and low power consumption for hand-held field applications. In particular, the present invention relates to a modular gas chromatography system which is capable of being interfaced with other portable analyzers.

2. Description of the Related Art

There has been a long-standing need for gas chromatography (GC) systems which are relatively small but have the capabilities and performance of full-size equipment. A desirable system would allow all of the individual components to be quickly attached and detached so as to allow interchange of components for different analyses. One early attempt at an improved GC system can be found, for example, in U.S. Pat. No. 3,403,545, the contents of which are incorporated herein by reference.

Over the years, several attempts have followed where size, weight, power consumption, heating/cooling, maintenance, speed and ease of use characteristics have been stressed. For example, in the commercial marketplace, there are a number of one or two-hand portable or larger GC systems. Each apparatus, however, has one or more undesirable features and/or cannot match the capabilities of most laboratory-sized systems that have a full range of state-of-the-art capabilities. Most commercially available field-portable GC devices are brief-case sized and hydrogen or helium is used as a carrier under isothermal GC conditions. One routine feature of full range systems is the ability to heat the GC in a systematic, controlled fashion while analyzing a sample. Hand-held GC systems, on the other hand, for example, lack temperature-programming capabilities for heating a sample. Thus, if the GC column had only a pre-set temperature and the compound of interest had a higher boiling point, then the compound would not elute from the column or it would creep along the column until it eventually eluted or decomposed. If a compound of interest has a higher boiling point than the GC column's pre-set temperature, the sample can be made to elute in a fairly straight-forward fashion by shortening the GC column, or increasing the flow rate of the gas through the column.

However, it is difficult and impractical to change the flow rate of the gas through the GC column in a linear fashion as is the case with temperature-programming. To elute various compounds with different boiling points at a pre-set GC column temperature, the flow rate of the gas through the GC column needs to be changed in an increasing fashion which means increasing the linear pressure difference across the GC column length. Increasing the pressure difference across the GC column in a linear fashion can be achieved in two ways: (1) increasing the pressure in the sampling end of the GC column or (2) decreasing the GC column length. The first approach is difficult and impractical for field-portable applications because the size of such apparatus would not fit within the palm of a hand. One pressure programmable assembly for GC columns requires a pressurized gas cylinder with a briefcase size pressure controlling unit. The second approach is completely impractical for portable GC's. In conclusion, it is undesirable to have a pressure-programmable GC column as well as a pre-set GC column temperature for field application purposes.

In view of the foregoing, improvements in hand-held GC systems have been desired. In addition to the lack of a temperature programming capability, it has been desired to provide GC systems which are smaller in size and have low power consumption needs.

The present invention addresses these needs.

SUMMARY OF THE INVENTION

In view of the foregoing, it is therefore an object of the present invention to provide a gas chromatography system which is hand-held and temperature programmable.

It is a further object of the present invention to provide a gas chromatography system having low power consumption requirements.

These and other objects are achieved by the present invention which includes a hand-portable, modular and temperature programmable gas chromatography module having reduced power consumption requirements. The GC module includes: a gas chromatography capillary column having a sampling and an effluent end; a sampling nozzle in fluid communication with the sampling end of the gas chromatography capillary column; a vacuum pulse generating means for generating a sample pulse and directing the sample pulse to the sampling end of the gas chromatography capillary column; an isothermal heating mantle; a resistive heating coil; a cooling fan; and a gas chromatography ring oven for housing the gas chromatography column.

In an alternative aspect of the invention, there is provided a portable and temperature-programmable gas chromatography module which includes a gas chromatography capillary column having a sampling end and an effluent end; an automated vapor sampling (AVS) means for generating a vapor sample and directing the vapor sample to the sampling end of the gas chromatography capillary column; and a programmable temperature control means including an isothermal heating mantle, an annular ring oven having a heating coil and housing a portion of the gas chromatography column, and a cooling fan. The annular housing is adapted for allowing the sampling end of the gas chromatography capillary column to receive the vapor samples from the automated vapor sampling (AVS) system and the effluent end of the column to release the vapor sample pulses to a secondary detection/analysis device.

In another aspect of the invention there is provided a GC system as described above in communication with a second portable analyzer and/or detector system such as an ion mobility spectrometer (IMS) system. For example, connection can be achieved linking the GC module of the present invention to an IMS device such as the hand-held Chemical Agent Monitor (CAM) system.

Some of the advantages of the GC module of the present invention include the fact that the module can be used in the field and can be hand-carried. The module can perform all functions of a full-size GC system while consuming small amounts of electrical power. Thus, the GC module is also suited for laboratory, industrial and medical research operations. Furthermore, the modular form of the GC apparatus of the invention can be readily connected to a regular IMS system such as the CAM.

GC module replacement is rapidly achieved due to the fact that the GC column is inside the GC module and is designed to be quickly connected and disconnected. Other and further advantages of the present invention are set forth in the description and appended claims.

DETAILED DESCRIPTION OF THE PREFERRED EMBODIMENT

In general, the GC module includes the following major units: (1) GC ring oven; (2) GC capillary column; (3) isothermal heating mantle; (4) cooling fan; (5) modified AVS device with sampling pulse plumbing assembly; (6) electronic circuits for temperature measurement and controls; and (7) means for connecting said device to a vapor sample input and means for interfacing the output of said device to a secondary analysis device.

In particular, the module includes: a gas chromatography capillary column having a sampling end and an effluent end; a sampling nozzle in fluid communication with the sampling end of a gas chromatography capillary column; a vacuum pulse generating means for generating a sample pulse and directing the sample pulse to the sampling end of the gas chromatography capillary column end; an isothermal heating mantle; a resistive heating coil; a cooling fan; and a gas chromatography ring for housing the gas chromatography column.

Figure 1:
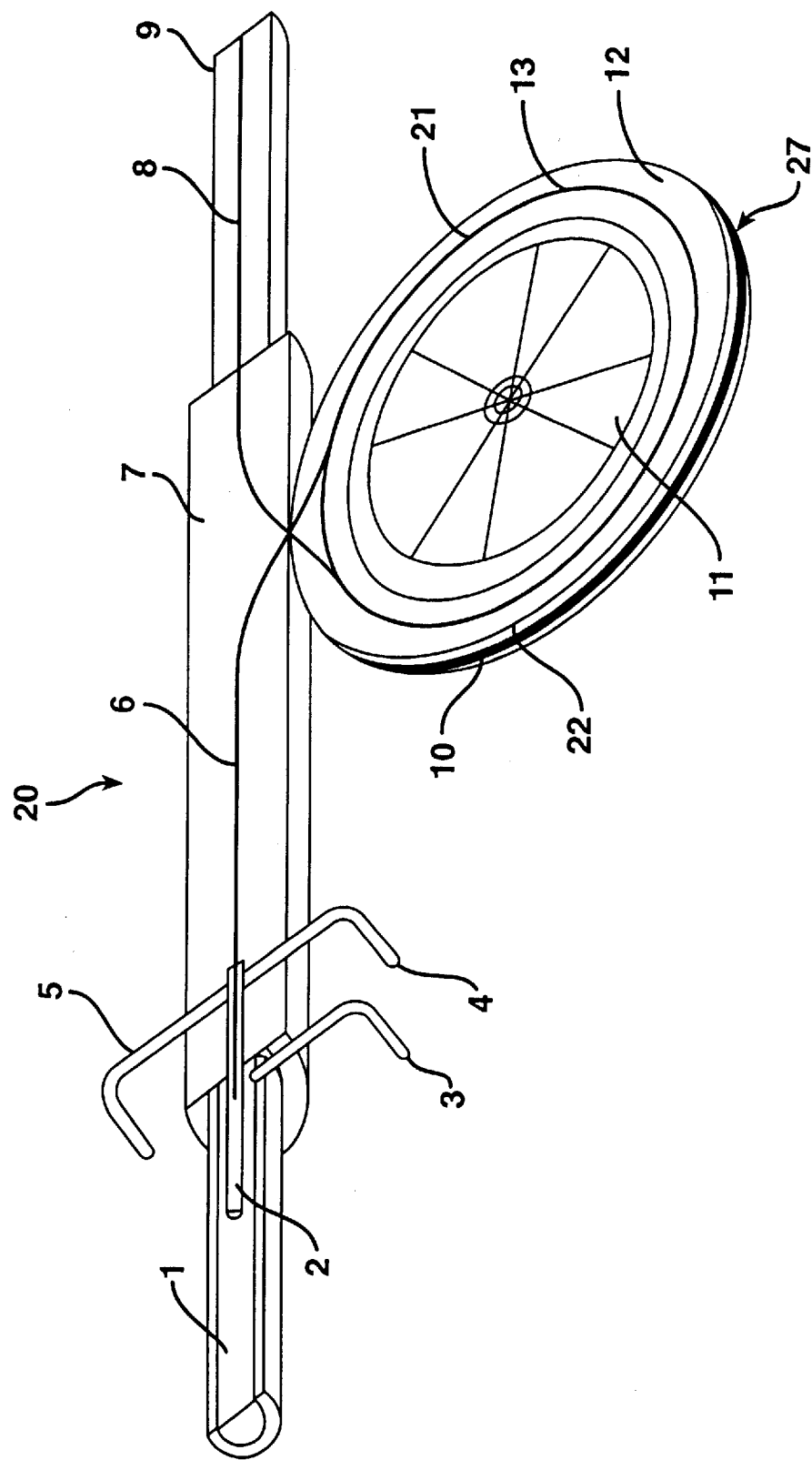
FIG. 1 is a cross-sectional view of a GC module in accordance with the present invention.

Referring now to the Figures, preferred aspects of the invention are illustrated. FIG. 1 presents a cross sectional view of a GC module 20 of the present invention. One device in accordance herewith has overall dimensions of about 9 cm in length, 6.5 cm in width and 4 cm in height (including insulation and support) and weighs about 160 grams. The GC ring oven 27 portion has an overall size of about 3.8 cm by 2.5 cm by 0.64 cm. FIG. 1 shows part of the modified AVS unit for vapor sample injection and includes a sample injection port 1, a valveless tube 2, programmed vacuum pulse connections 3 and 4, and air flow tube 5. This combination of elements constitutes part of a modified automated vapor sample (AVS) introduction system which operates in combination with the plumbing scheme set forth in FIG. 4 to generate a pulse. The miniature cooling fan 11 is included with the system for forced air cooling and is placed below the GC ring oven 27. The fan 11 is utilized to force cool air through the module and allow rapid cooling of the column 13 as necessary, or desired.

The GC module preferably includes a modified AVS introduction system and the module operates in both stand-by mode and sample injection mode. The modified AVS consists of the sample injection port 1, the valveless tube 2 and the programmed vacuum pulse connections 3–5. The programmed vacuum pulse is initiated by the single 3-way valve plumbing scheme of FIG. 4. During stand by mode, sample air is taken into the GC module from the ambient environment through the sample injection port 1. The sample air flow is then drawn out through the vacuum pulse connection 3. The vacuum pulse connection 3 pulls the air-analyte flowing inside the sample injection port 1. The vacuum can be drawn by any suitable and commercially available miniature vacuum pump. The sample air flow is then drawn through the system of FIG. 4 where it is cleaned, dried and cycled back as a carrier gas, (no bottled gas supply is used) via air flow tube 5. The clean dry air then flows out of the valveless tube 2, and the vacuum connection 4. Finally, any remaining portion of the clean dry air flow is directed to the GC capillary column sample end 6 for flow through the GC capillary column.

In sample injection mode, sample air is similarly drawn into the sample injection port 1, is then directed to the valveless tube 2 where a portion is drawn to the vacuum pulse connection 4 and a portion of the flow is directed to the GC capillary column sample end 6 for flow through the GC capillary column. During sample injection mode, the vacuum pulse connection 4 directs the air-analyte flowing inside the sample injection port 1 through the valveless tube 2 to the GC capillary column sample end 6; with the remainder of the sample air being drawn through vacuum pulse connection 4 and being recycled as clean dry air at tube 5.

Figure 4:
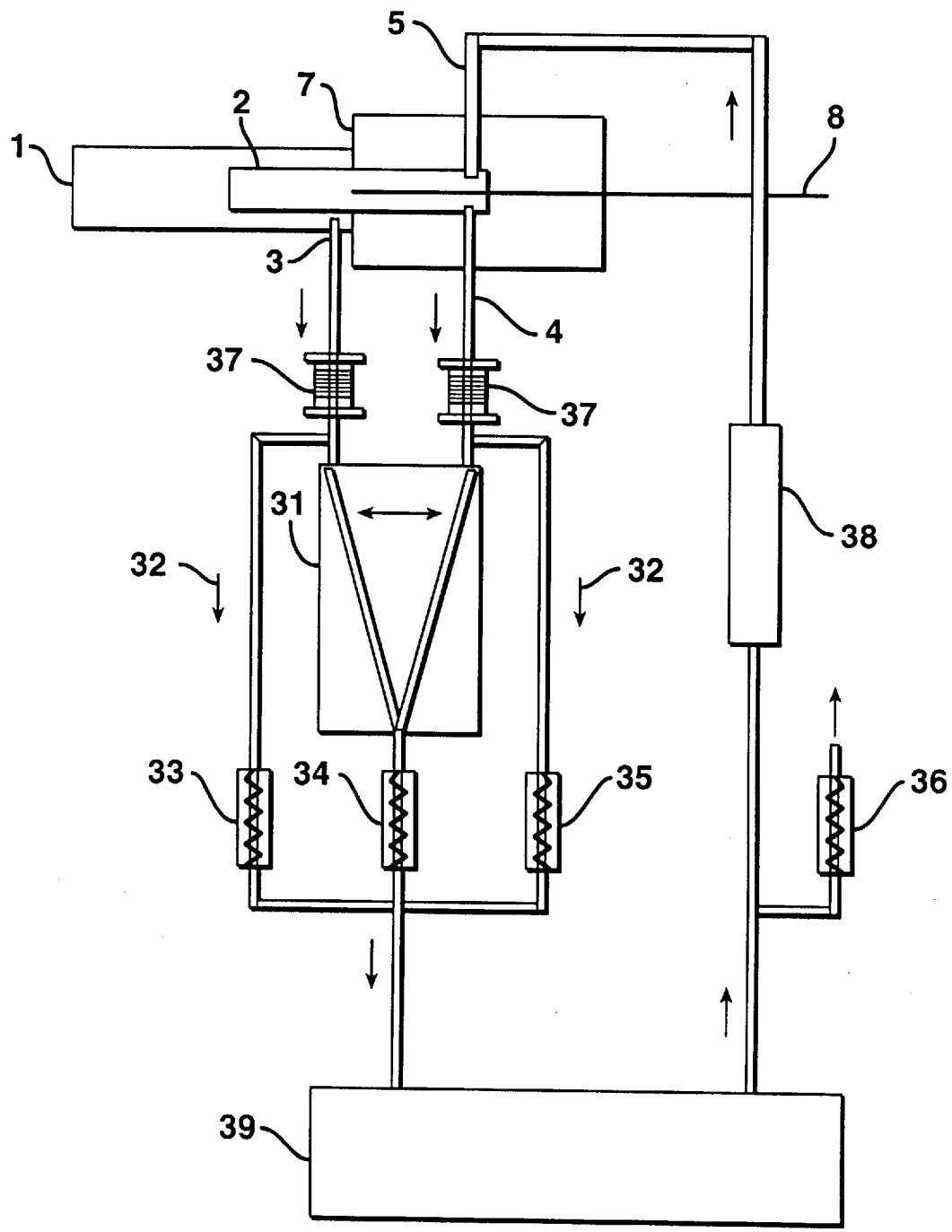
FIG. 4 is a flow diagram illustrating a three-way valve plumbing scheme in a modified sampling pulse plumbing assembly.
Figure 5:
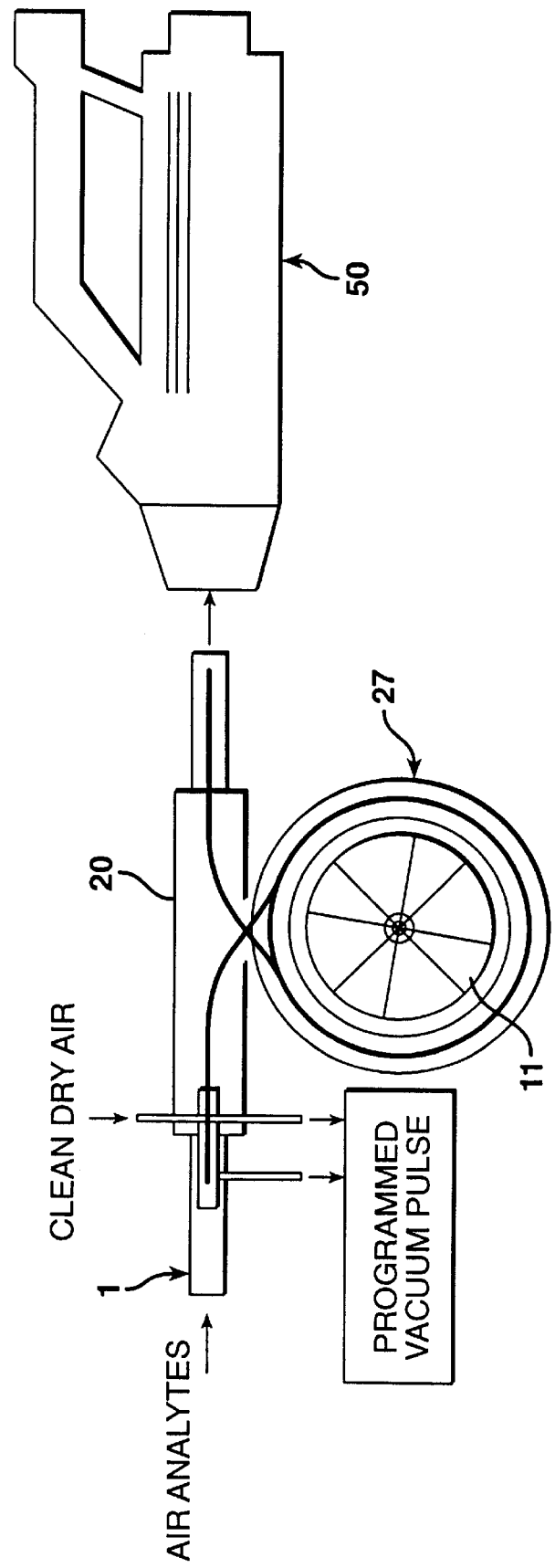
FIG. 5 illustrates a further embodiment of the invention in which the GC module is connected to a hand-held ion mobility spectrometer (IMS) system such as the CAM.

FIG. 4 also shows that the small fraction of the air sucked through the programmed vacuum pulse flow restrictors 33–35 is cleaned and dried via a charcoal filter unit 38 while the rest is vented out via the vent flow restrictor 36. The recycled clean, dry air from the charcoal/filter unit 38 is used to protect the sampling end of the GC column during stand by operations from the outside air analyte. A small fraction of that recycled clean, dry air is used as a carrier gas which flows inside the capillary GC column due to the pressure difference between the sampling and effluent end of the GC column.

The gas chromatograph module 20 is used in connection with a modified AVS having a sample collector/injector system 1–5 for introducing a sample into the module 20. During sample injection mode, the introduced sample passes through a valveless tube 2 and programmed vacuum pulse connection 4 where the introduced sample passes into the GC capillary column sampling end 6, through the temperature controlled isothermal heating mantle 7 and eventually to the gas chromatograph column assembly 13 and to a detector port 9 for transmitting and for registering the sample components and sending data to an output device such as a PC notebook computer. The AVS detector mantle portion comprising elements 1–9 are controlled at an isothermal temperature using the software-based controls discussed below.

The sample collector/injector portion of the module 1–5 is illustrated in the figures as an example only. Other configurations employing the gas chromatograph module 20 are possible. Such alternate configurations include gas chromatograph systems incorporating inlets configured for syringe injection of the sample; gas chromatograph systems incorporating inlets configured for purge and trap or head space analysis; gas chromatograph systems adapted for accepting pyrolysis products; and gas chromatographs configured for the use of autosamplers.

Figure 2:
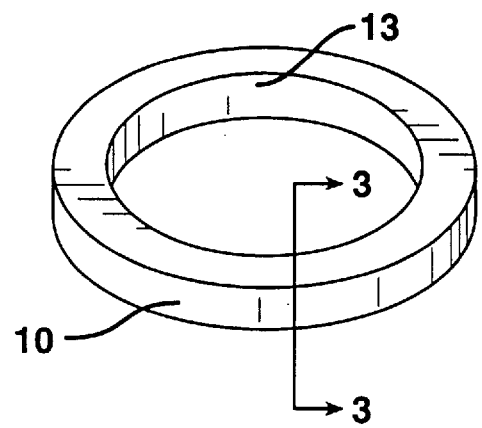
FIG. 2 is a schematic diagram of the GC ring oven used in the GC module.
Figure 3:
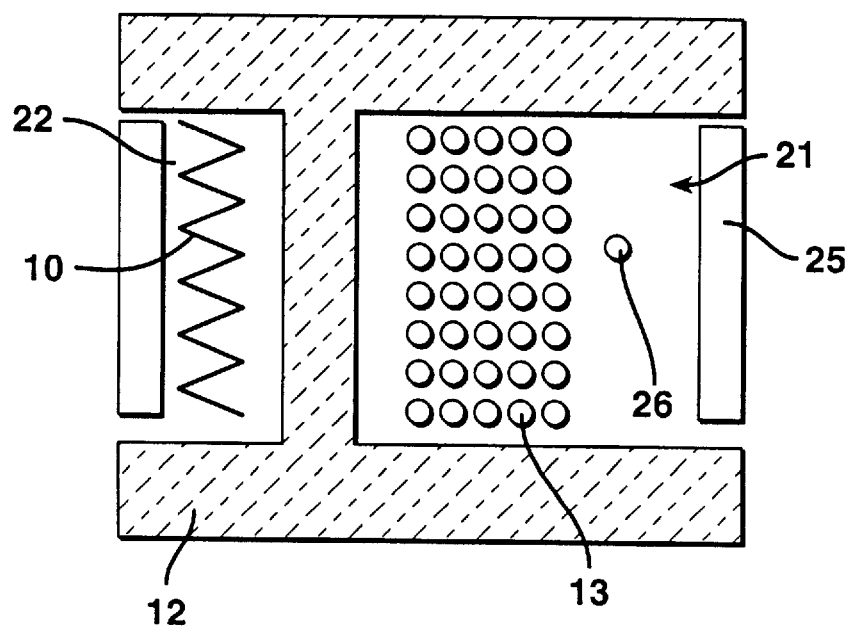
FIG. 3 is a cross-sectional view of the GC ring oven taken along line 3—3.

The GC ring oven 27 includes a ring housing 12 which can be an aluminum ring with a first groove 21 in the inner circumference and a second groove 22 in the outer circumference as shown in FIGS. 1, 2, and 3. The GC capillary column 13 is coiled inside the inner groove 21 with an insulating layer 25 and a thermocouple 26 for controlling the heating of the column. The heating element 10, which can be simply a resistive wire, is wrapped around the outer groove 22. The GC column used can be a standard fused silica capillary column such as a DB1, 1 m×0.25 mm ID column available from J&W Scientific, Falsom, Calif. This column is coated with polyimide (non-electrically conductive film) on the outside and 0.25 micron DB1 liquid phase.

The ring design is preferred because the GC ring oven 27 has low heat mass and maximum surface area per unit volume which allows for fast heating and cooling rates, low power consumption, small size and light weight. The capillary GC column 13 is naturally coiled inside the ring housing 12 while the two column ends, i.e the sampling end 6 and the effluent end 8 are pointed out in the opposite directions. The two GC capillary column ends, that is, the sample end 6 and effluent end 8, are extended in a substantially straight line so that one end is connected to the sample injection port 1 via a valveless tube 2 and a programmed vacuum pulse connections 3 and 4 as part of a modified automated vapor sampling (AVS) introduction system. The automated vapor sampling (AVS) unit was found to offer the desired miniature characteristics needed for the palm size GC module 20. Some of the desired characteristics of the AVS are: 1) easily constructed; 2) miniature size; 3) low power consumption; 4) internal surfaces that are deactivated fused silica; and 5) operating temperature up to 300°. A modified AVS unit, see FIG. 4, was integrated with the GC oven 27 and the GC capillary column effluent end 8 in a way to eliminate the cold spots and reduce the power consumption as well as overall size. In operation, the AVS allows the GC column inlet sampling end 6 to be swept by clean, dry air during standby operation and by the vapor sample during the sample injection. Air flows in the AVS unit are fixed by using a single 3-way valve plumbing scheme with a miniature vacuum pump 39 as shown in FIG. 4. For example, one such pump is available from Schwarzer Prazision as Model SP 135 FZ, 4.5VDC. When the GC module is integrated with an ICAM system, the miniature vacuum pump 39 need not be used because the ICAM dual air pump will draw the required vacuum. The GC capillary column effluent end 8 is connected to a fitting 9 for rapid connection to another detector such a non-dimensional detector or a one-dimensional (of information) spectrometer detector.

A computer program generates the necessary time-controlled signals to control different parts of the GC module (e.g., 3-way valve AVS/detector mantle isothermal temperature, temperature history profile of the GC ring oven, fan, etc. The program also acquires and displays all the signals (temperature measurements, temperature histories, injection pulse times, etc.) from the GC module on to the computer monitor/screen (not shown) as well as saves the acquired signals into a single file. The temperature history of the GC oven can be changed into any simple or complex temperature history by changing the analog output wave function of the data acquisition PCMCIA card (DAQCard-1200, National Instruments.) See FIG. 6. The analog output signal is connected to a complete instrumentation monolithic thermocouple amplifier with cold junction compensation chip (ANALOG DEVICES, AD595, Norwood, Mass.) A combination of monolithic thermocouple amplifiers (AD595) and solid state relays are connected to the heating element and type K thermocouples of the GC oven as well as AVS/detector port mantle for temperature control and measurements. The electric circuit example of the monolithic thermocouple amplifier used can be found in the ANALOG DEVICES reference handbook, signal conditioning components, chapter 10, Published by Analog Devices (1994), the contents of which are incorporated herein by reference. A constant heating rate was obtained in the GC ring oven by applying a defined voltage ramp on the set-point voltage input connection of the monolithic thermocouple amplifier chip which translated into a constant rate of changing set-point temperature in time. The translation is very fast, usually less than one microsecond.

The modular GC device consists of two parts which are a quick connect/disconnect in design. The top part consists of the GC oven ring 27, the AVS device 1–5 FIGS. 1 and 4, and the GC isothermal heating mantle 7, which is the disposable part. The bottom part consists of a cooling fan, a single 3-way valve/plumbing scheme, a miniature vacuum pump and the electrical components. The bottom part can also be either recycled or disposed.

The GC module and the ICAM device are controlled and operated using a DAQCard-1200 multifunction I/O board (National Instruments Corporation, Austin, Tex.). Algorithms for the GC-IMS system were written using LabWindow/CVI software version 3.1 (National Instruments, Austin, Tex.) for data collection, temperature measurement and control and other functions. Software was written to acquire, save and display the IMS spectral signal with low and high collection rate modes. A high data collection rate (>10 spectra/sec) is necessary to resolve the GC peaks of less than 0.5 second half peak width.

In summary, the GC module is driven and controlled by a computer program which is user-friendly, preferably graphically driven and can be made using a National Instruments software package.

Direct current is used to heat the GC ring housing 12 and column 13 inside. Different heating rates are obtained by applying different voltage ramps on the AD595 chip circuit that automatically turn the voltage across the heating element 10 (resistive wire wrapped around aluminum GC ring) to a new set-point temperature in time:

$V - V_o = at + b$ where $V_o$ is the applied voltage at time 0, V is voltage as a function of time (t) and (a) and (b) are calibration constants. The approach used here of varying set-point temperature by controlling the on/off voltage across the heating element 10 is to minimize the power loss through electronic components and control devices. Using direct current with changing set-point temperature approach is preferred because direct current heating is the most efficient way of heating, i.e. more that 95% (estimated) of consumed electrical power will go toward heating the GC housing 12 and GC column 13.

FIG. 4 schematically shows the compact plumbing approach used to control flow rates inside the modified AVS device comprising elements 1–5, and produce a near square wave injection pulses. The compact plumbing uses a single, miniature 3-way valve 31, continuous bleed flows on the vacuum sides 32, flow restrictors 33, 34, 35 and 36, prefilters 37 to clean the incoming air-analyte before it passes to other units (e.g., 3-way valve), charcoal filter 38 to clean and dry the vacuumed incoming air-analyte and produce the carrier air going to AVS unit and through the GC column 13 and baked viton tubes used for connecting various elements. This 3-way valve plumbing scheme used to generate the AVS square sampling pulse differs from the plumbing scheme used on the AVS device disclosed in U.S. Pat. No. 4,970,905 since the module of the invention includes a 3-way miniature solenoid valve 31 that offers consistent operation, low power consumption (from about 0.2 to about 1.0 Watt, and preferably about 0.28 Watt) and rapid response time (i.e from about 1.0 to about 5 ms, preferably about 1.5 ms). One such valve is available from the Lee Company (LFAA series, Westbrook, Conn.). Flow restrictors 33–66 are preferably in the shape of capillary S.S. tubes (1/16"× 0.007" i.d., Alltech Associates, Inc, Deerfield, Ill.) of selected lengths and used to set the flow rates.

In one aspect of the invention, there is provided a temperature programmable, disposable GC module that performs most functions of a full size GC system. The GC modules of the present invention are essentially maintenance free, compact, disposable, quick connecting and disconnecting. Unlike prior art GC systems which are large and have relatively large power requirements to operate, the GC module of the invention is a single unit, small in size, light weight with low power consumption, thus making the device suitable for field applications and screening. Furthermore, unlike commercially available portable systems which have isothermal operating conditions, the GC module of the present invention is designed to include programmable heating and cooling capabilities as well as perform all functions of a full size GC system with minimal consumption of electrical power, consuming about 8 watts during heating and a total of about 15 watts of electrical power during a typical GC analysis. The inventive device also has relatively rapid cooling rates (time constants of about 36 seconds being preferred) to reduce down time. In addition, the leaks inherent in commercially available portable or full-size GC column connections are avoided with the modules of the present invention. Finally, the sample injection and interface connection difficulties of prior art GC systems are avoided with the GC module of the present invention. The number of interface connections are reduced to two. The sample injection and the detector or the GC effluent port are integrated into one mantle, as shown in FIG. 1 see 1–9. The integration into one heated mantle eliminates the inherent cold spots or over-heating between the different heated zones of prior art GC systems. Also, the integration has reduced not only the power consumption significantly but also the number of connections/interfaces that might have potential air leaks. Furthermore, by integrating the two units, the GC oven portion 27 (which embodies 10 through 13) and the AVS/detector port mantle portion (1 through 9 in FIG. 1) into one unit which is the disposable subunit of the GC module 20. There will be, therefore, no need to replace the GC column, sample injector parts and connecting ferrules that might result in leaks or difficulties. The disposable subunit is easily connected and disconnected over the recycled subunit. The detector port 9 is connected to a detector by sliding into an O-ring or swagelock fitting. The sample injection difficulties were avoided by using the AVS device which automatically admits a pulse of air analyte in the ambient air into the GC sampling end without using a manual needle and/or trap/desorb injection.

In another preferred embodiment of the invention, an ion mobility spectrometer (IMS) detector system such as a regular Chemical Agent Monitor (CAM) is converted to a GC-IMS system with a simple conversion kit that includes the GC module. The GC module separates ambient air analytes or vapors according to their chromatographic capacities to provide identification of the analytes or samples.

In a preferred aspect of the invention, the GC module is connected to a secondary detection apparatus. Some of the advantages of interfacing a GC column with a spectrometer (e.g., MS, FTIR, IMS, etc.) detector includes the fact that a spectrometer detector gives a second identification dimension to the GC detection dimension. Such an interface is more popular in laboratory environments because the interfaced units such as GC-MS and GC-FTIR (Fourier transform infrared) are relatively heavy, large in size, and consume a lot of electrical power. The present invention, on the other hand, allows this tandem-type analysis to be carried out in the field using portable equipment. It will be understood, however, that the advantages of interfacing a GC system to an IMS system will be balanced by factors such as (1) co-eluting peaks, (2) size, (3) weight, (4) cost, (5) power consumption, (6) maintenance requirements, (7) ease of replacement, (8) database, (9) identification efficiency, (10) selectivity, (11) resolution, (12) analysis time and (13) versatility. To resolve a co-eluting peak which consists of compounds that are different in chemical nature, it may become necessary to change 1) the capillary GC column stationary phase type, and 2) the selective detector, and/or use a deconvolution algorithm.

Some of the advantages of the compact, disposable GC module of the present invention are that the module can be used in the field and that module was designed and constructed to perform all functions of a full size GC system with the least amount of electrical power consumption. The AVS/GC unit in a modular form can be easily hooked up to a regular ion mobility spectrometer (IMS) chemical agent monitor system (CAM).

Figure 6:
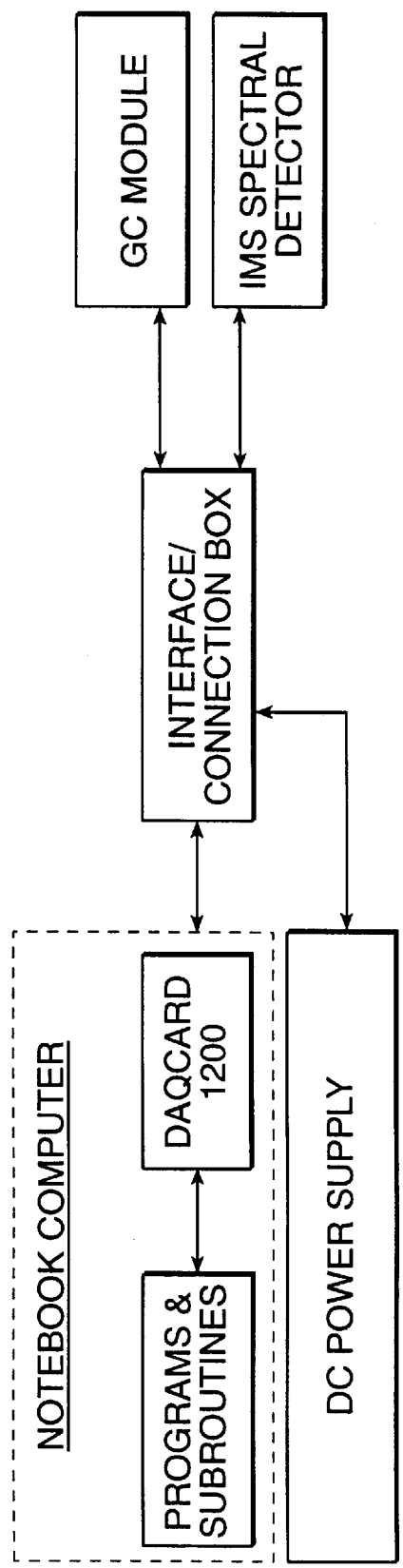
FIG. 6 is a flow chart diagram of the different components used with the GC module.

As an illustrative example, reference is made to FIG. 6. The GC module is shown in combination with a notebook computer, an ICAM (improved chemical agent monitor), an (IMS) detector, and a power supply (small battery; 6V DC, 12 hr.A). In particular FIG. 6 shows a schematic diagram of the GC module being connected to a regular ICAM (detector) and controlled by a notebook computer. The Example and Tables below show the operating parameters used in the GC module and ICAM detector. Because a regular ICAM operates in air, the carrier gas used in the GC module was simply clean, dry air.

EXAMPLE

Dimethyl methylphosphonate (DMMP), Diethyl ethylphosphonate (DEEP), Trimethylphosphite (TMPI), Triethylphosphite (TEPI), Diaminobutane (Putrescine), Diaminopentane (Cadaverine) and 2,4-lutidine were purchased from Aldrich (Milwaukee, Wis.) and used with further purification.

Different steady state analyte concentrations (PPM to PPT) of vapor samples were generated using a Q5 vapor generator. The Q5 operates by diluting a stream of saturated sample vapor with dry, clean air to various degrees.

RESULTS AND DISCUSSIONS

Figure 7:
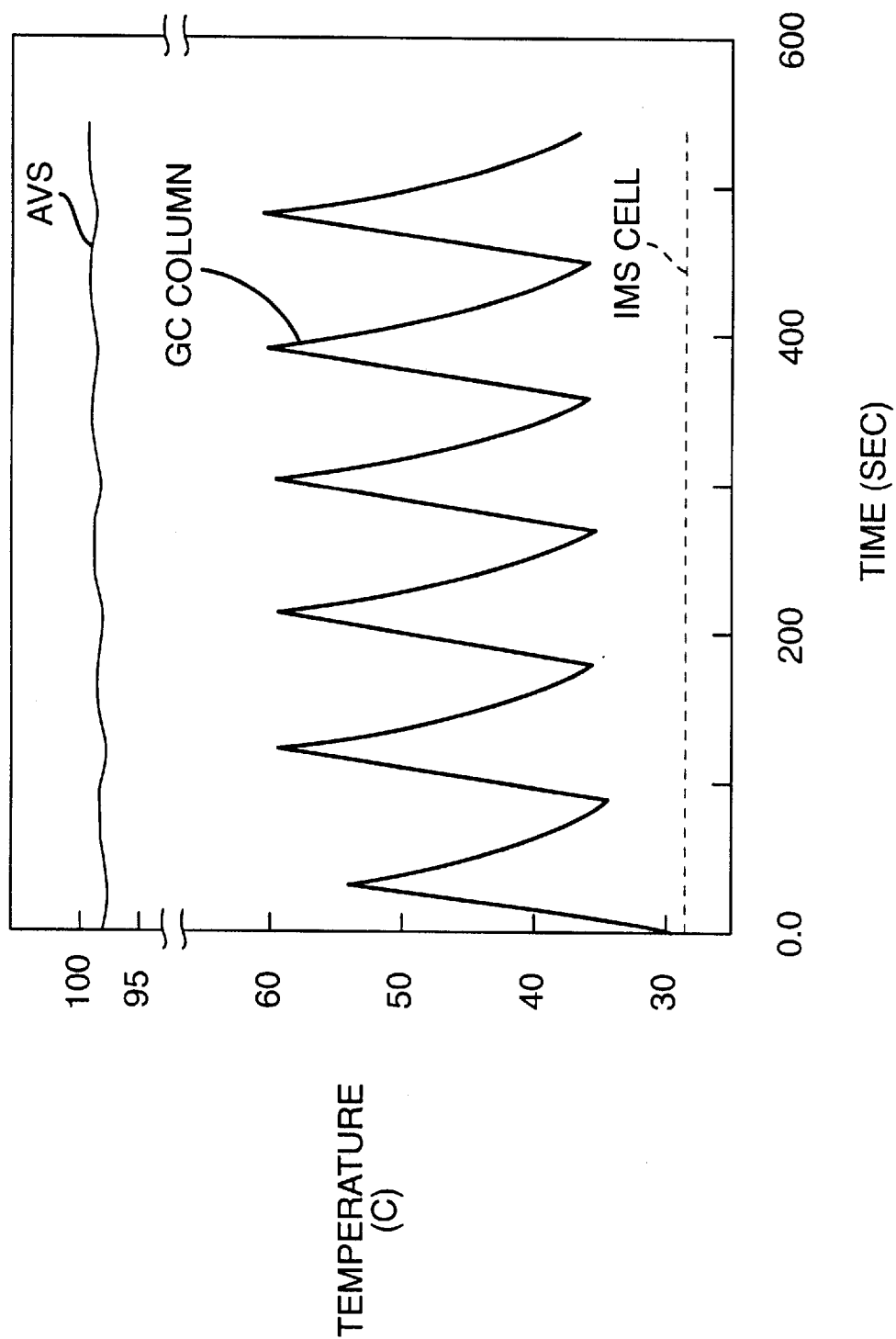
FIG. 7 graphically illustrates the temperature history of an automated vapor sampling (AVS) sample introduction system and GC assembly under repetitive heating/cooling cycles.

FIG. 7 shows typical AVS/GC outlet mantle and GC column temperature histories. The AVS/GC outlet mantle was maintained at an isothermal temperature of about 95° C. The GC column was set to cycle at a constant heating rate of 45° C./min for 30 seconds and cool down for 60 seconds. Cooling was effected by a small fan (5V DC, 170 mA) placed under the GC oven. The cooling time constant is 36 seconds when evaluated at room temperature. Typical experimental conditions used for the modular GC-IMS system are shown in Table 1.

TABLE 1

OPERATING CONDITIONS FOR GC/IMS SYSTEM

| | |
|---|---|
| Weight (g): | 160 |
| Power Consumption (W): | 15 heating; 6 cooling |
| Liquid Phase: | DB-1 (0.25 μm) |
| Temperature °C./min: | 45 (program) |
| Carrier Gas: | clean dry air |
| Flow Rate (ml/min): | 2.1 |
| Length (m): | 1.0 |
| Sample Injection Pulse (sec): | 0.2–1.0 (select) |
| AVS Temp. (°C.): | 90 |

ION MOBILITY SPECTROMETER

| | |
|---|---|
| Power Consumption (W): | 3 |
| Ionization Source: | $^{63}$Ni |
| Gating Pulse Rate (Hz): | 30 (internal) |
| Drift Gas: | Clean, dry air |
| Mode: | Positive ions |
| Cell temperature: | 30 |
| Cell pressure: | 640 |

The total power consumption of the GC/IMS system for a typical run is 18 watts GC column heating. Average power consumption is calculated as follows:

$$\text{Average Wattage} = 18t_{heat} + 9t_{cool})/(t_{heat} + t_{cool})$$

$t_{heat}$: heating time and $t_{cool}$: cooling time.

FIG. 7 shows a temperature history of the modified AVS, GC capillary column inside the GC module of the invention and the IMS Cell during repetitive 30 second heating (45° C./min) and 60 second cooling cycles. Note the repeatability and reproducibility. The GC module can be optimized for certain application(s) of interest by choosing the proper heating rate and the heating-cooling frequency (heating and cooling periods). The optimum GC column cycling temperature history is at which maximum chromatographic separation and resolution is attained for compounds of interest. The heating-cooling cycles reduce the analysis time and can be used as a monitoring technique.

Figure 8:
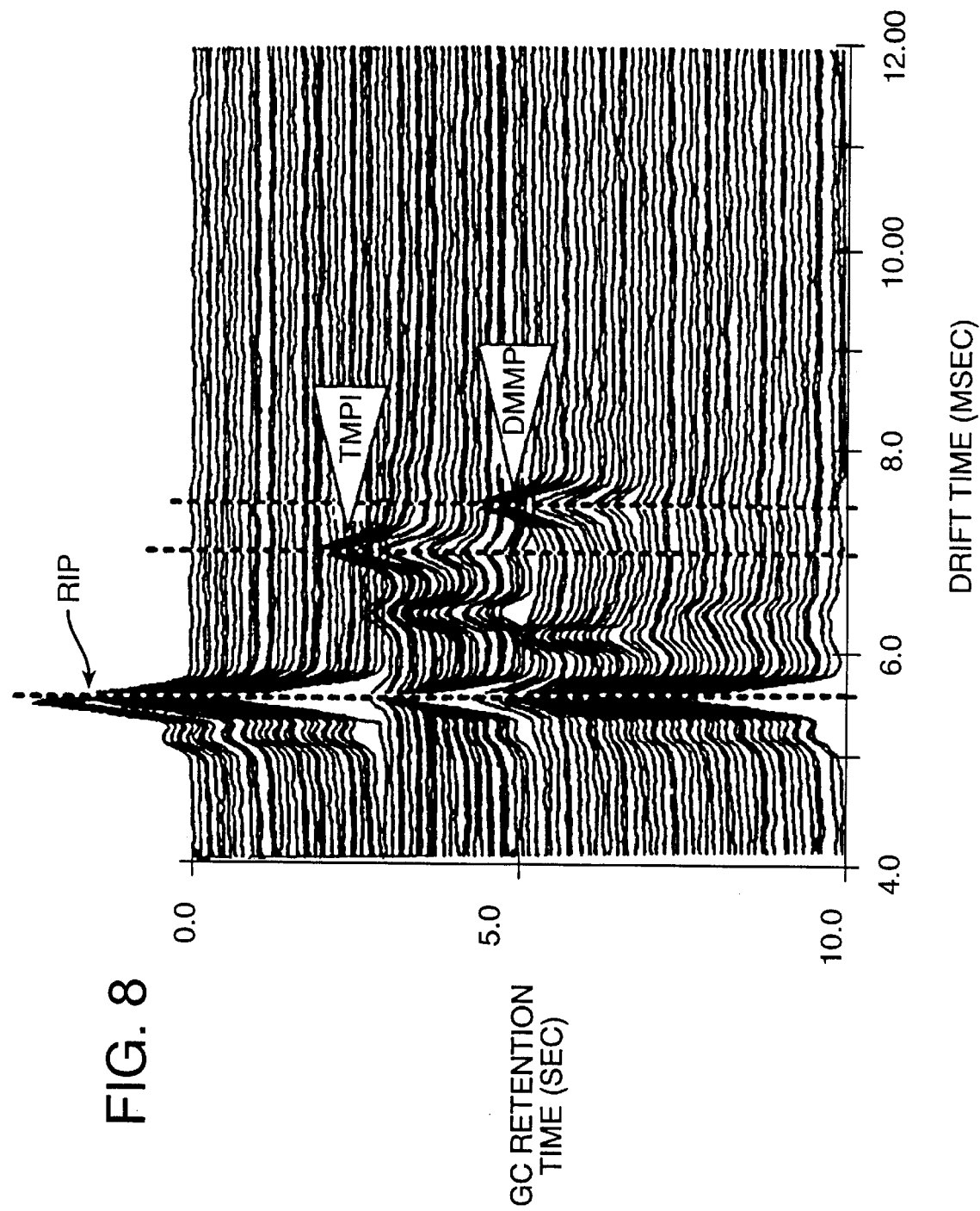
FIG. 8 illustrates data obtained using an apparatus of the present invention in communication with an ion mobility spectrometer showing a water-fall plot of trimethyl phosphite and dimethylmethylphosphonate.
Figure 9:
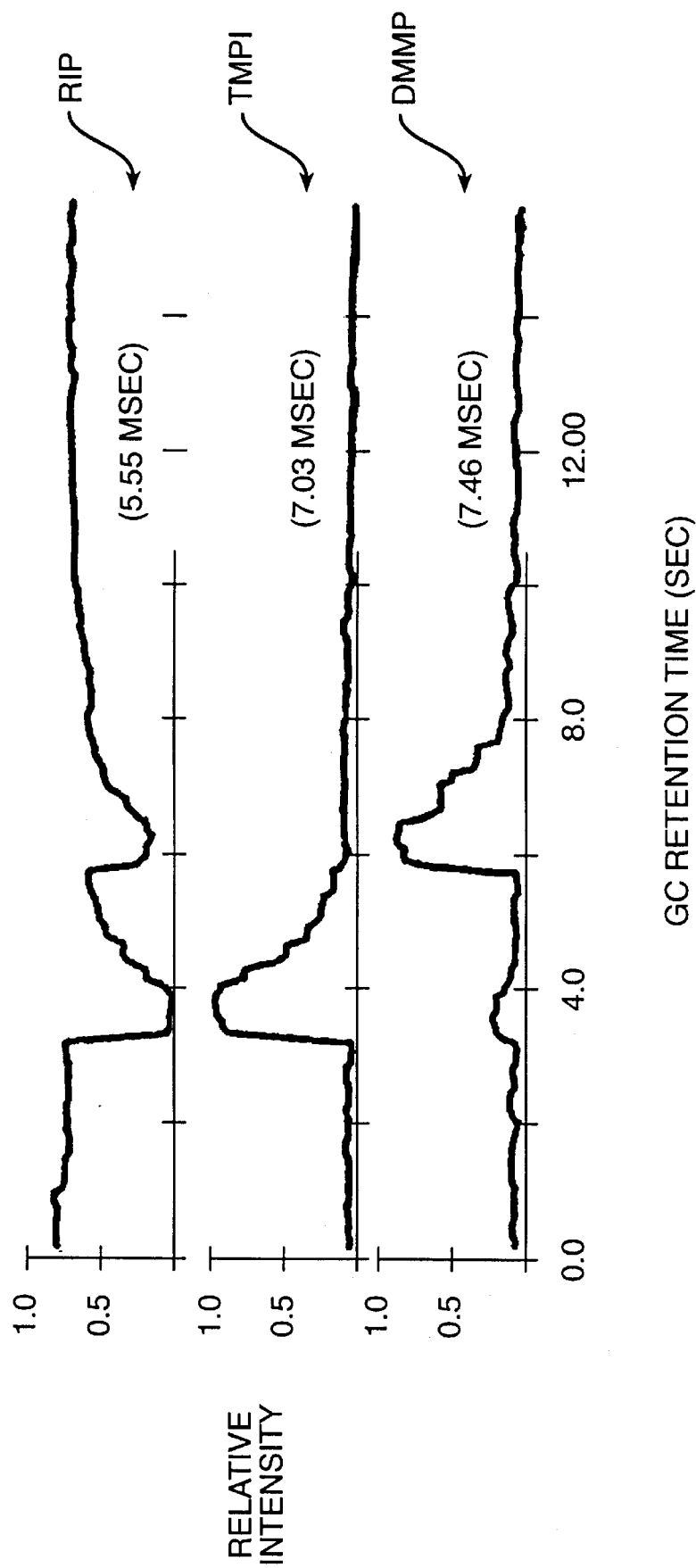
FIG. 9 illustrates selected ion mobility chromatograms obtained as a result of the GC module of the present invention being connected to an ion mobility spectrometer.

Trimethylphosphite (TMPI) headspace vapor was analyzed and displayed in a "water fall" format as shown in FIGS. 8 and 9. Two components were separated through the GC column, TMPI and dimethyl methylphosphonate (DMMP) because TMPI exists in equilibrium with DMMP. Note the short analysis time (approximately 6–7 seconds) separates a mixture of a phosphonate and a phosphite. FIG. 9 shows selected ion mobility chromatograms of the reactant ion peak (5.55 msec), TMPI dimer ion peak (7.03 msec) and DMMP dimer ion peak (7.46 msec). Selected ion mobility chromatograms show peak tailing which indicates a dead volume in the IMS system, originating in the ionization region. Other organophosphorous compounds were also analyzed by the GC-IMS system. Table 2 below shows selected organophosphorous compounds analyzed by the GC-IMS system. The values listed in the drift time and reduced ion mobility constant ($K_o$) columns are for the monomer and dimer ion peak, respectively. The reduced ion mobility constants ($K_o$) are calculated using a 2,4-lutidine monomer ion drift time of 5.92 msec and a standard reduced ion mobility constant of 1.95 cm/V.sec as follows:

$$(K_o t_d)_{sample} = (K_o t_d)_{lutidine}$$

where $t_d$ is the drift time.

TABLE 2

| chemical name | MW | bp (°C.) | retention time (sec) | Drift time (msec) | $K_o$ cm/V .sec |
|---|---|---|---|---|---|
| trimethyl- | 124 | 112 | 3.30 | 6.40 | 1.80 |
| phosphite | | | | 7.03 | 1.64 |
| dimethyl | 124 | 181 | 5.90 | 6.18 | 1.86 |
| methylphos- | | | | 7.46 | 1.54 |
| phonate | | | | | |
| triethyl | 166 | 156 | 9.0 | 6.77 | 1.70 |
| phosphite | | | | 8.19 | 1.41 |
| diethyl ethyl- | 166 | 82 | 20.6 | 6.81 | 1.69 |
| phosphonate | | | | 8.93 | 1.29 |
| 2,4-lutidine | 107 | 159 | 8.30 | 5.92 | 1.95 |
| | | | | 7.58 | 1.52 |

FIG. 9 shows a typical GC-IMS chromatogram of a sample of trimethylphosphite (TMPI). Note the level of separation between TMPI and the DMMP (Dimethyl methylphosphonate) impurity and the relatively fast analysis time. Same design approaches and concepts can be applied to construct compact, disposable liquid chromatograph (LC) modules. Liquid chromatography could benefit from the GC module design concepts greatly by: 1) using a circular column design (e.g., ring oven design) for reducing overall size; 2) integration of the sample injection inlet with the detector; and 3) 3-way valve plumbing scheme to clean, dry carrier solution, among others.

While the invention has been described in connection with preferred embodiments, it will be understood that it is not intended to limit the invention to these embodiments. On the contrary, it is intended to cover all alternatives, modifications, and equivalents as may be included within the spirit and scope of the invention defined in the appended claims.

What is claimed is:

1. A gas chromatography module, comprising:

a gas chromatography capillary column having a sampling end, an effluent end, and a coiled section intermediate said sampling end and said effluent end;

oven means for controlling the temperature of said gas chromatography capillary column, including a cylindrical housing, and means defining a circumferential groove in said cylindrical housing;

said coiled section of said gas chromatography capillary column being disposed in said circumferential groove of said cylindrical housing;

said oven means including heating means for heating said cylindrical housing to thereby heat said gas chromatography capillary column;

a first fluid conduit means surrounding said sampling end of said gas chromatography capillary column;

a second fluid conduit means surrounding said first fluid conduit means;

vacuum pump means for directing an airflow from said first fluid conduit means into said second fluid conduit means during a stand-by mode; and vacuum pulse generating means for influencing said airflow to thereby control the application of a vapor sample through said first fluid conduit means into said sampling end of said gas chromatography capillary column.

2. The gas chromatography module of claim 1 wherein:

said first fluid conduit means is a tube having an open forward end which extends forward of said sampling end, and having a rearward end; and said rearward end has a fluid conduit input from an output of said vacuum pump means; and said rearward end has a fluid conduit output to an input of said vacuum pump means.

3. The gas chromatography module of claim 2 wherein:

said second fluid conduit means is a tubular sample injection port having an open forward end which extends forward of said first fluid conduit means, and having a rearward end; and said rearward end has a fluid conduit output to an input of said vacuum pump means.

4. The gas chromatography module of claim 3 wherein:

said vacuum pulse generating means includes a three-way valve means selectively connectable to each of said fluid conduit outputs for changing the flow rate therethrough to thereby selectively enable the stand-by and sampling modes.

5. The gas chromatography module of claim 2 further including:

means for cleaning and drying the airflow through said fluid conduit at the rearward end of said first fluid conduit means.

6. The gas chromatography module of claim 1 further including:

means for connecting said effluent end to a secondary detection device.

7. The gas chromatography module of claim 6 wherein:

said secondary detection device is a spectrometer.

8. The gas chromatography module of claim 1 wherein:

said cylindrical housing has a ring configuration;

said circumferential groove being in an inner circumference of said housing;

further including means defining a circumferential groove in an outer circumference of said housing; and said heating means being a resistive wire disposed within said outer circumferential groove.

9. The gas chromatography module of claim 1 further including:

programmable means for controlling the temperature of said gas chromatography column.

10. The gas chromatography module of claim 9 wherein:

said programmable means includes an isothermal heating mantle.

* * * * *